(12) United States Patent
Yamakawa et al.

(10) Patent No.: US 7,727,470 B2
(45) Date of Patent: Jun. 1, 2010

(54) ANALYZER AND ANALYZING SYSTEM

(75) Inventors: Nobuyoshi Yamakawa, Kobe (JP); Hiroyuki Tanaka, Kobe (JP)

(73) Assignee: Sysmex Corporation, Hyogo (JP)

( * ) Notice: Subject to any disclaimer, the term of this patent is extended or adjusted under 35 U.S.C. 154(b) by 1362 days.

(21) Appl. No.: 10/890,878

(22) Filed: Jul. 14, 2004

(65) Prior Publication Data

US 2005/0036912 A1 Feb. 17, 2005

(30) Foreign Application Priority Data

Jul. 15, 2003 (JP) ............................. 2003-196907

(51) Int. Cl.
*G01N 21/00* (2006.01)
(52) U.S. Cl. .......................................... 422/67; 436/47
(58) Field of Classification Search ................... 422/67, 422/50; 436/50, 55, 47
See application file for complete search history.

(56) References Cited

U.S. PATENT DOCUMENTS

| 5,209,903 | A | 5/1993 | Kanamori et al. | |
|---|---|---|---|---|
| 6,019,945 | A * | 2/2000 | Ohishi et al. | 422/65 |
| 2002/0016683 | A1 * | 2/2002 | Shiba et al. | 702/22 |

FOREIGN PATENT DOCUMENTS

| JP | 02-179477 | 7/1990 |
|---|---|---|
| JP | 07-120476 | 5/1995 |
| JP | 7-239333 | 9/1995 |
| JP | 07-280814 | 10/1995 |
| JP | 11-094838 | 4/1999 |
| JP | 11-148940 | 6/1999 |
| JP | 11-237384 | 8/1999 |
| JP | 2001-296911 | 10/2001 |
| JP | 2003-066050 | 3/2003 |
| JP | 2003-066053 | 3/2003 |

* cited by examiner

*Primary Examiner*—Jill Warden
*Assistant Examiner*—Natalia Levkovich
(74) *Attorney, Agent, or Firm*—Brinks Hofer Gilson & Lione

(57) ABSTRACT

Analyzers are described that includes a first conveyance device for transporting a container accommodating analyte; a first analyzer body for analyzing analyte accommodated in a container transported by the first conveyance device; a first transmission device for transmitting a first information through a first path from the first conveyance device to a predetermined computer; a second transmission device for transmitting a second information through a second path from the first analyzer body to the predetermined computer without passing through the first conveyance device; and setting device for setting whether or not to transmit the first information to the predetermined computer.

Analyzing systems are also described.

9 Claims, 9 Drawing Sheets

Fig.5 Flow of maintenance information transmission by the first conveyance

ANALYZER AND ANALYZING SYSTEM

RELATED APPLICATIONS

This application claims priority under 35 U.S.C. §119 to Japanese Patent Application No. 2003-196907, filed Jul. 15, 2003.

FIELD OF THE INVENTION

The present invention relates to an analyzer and analyzing system, and specifically relates to an analyzer which transmits information to a computer, and analyzing system.

BACKGROUND

In recent years the quantity of information transmitted from examination systems and analyzing systems to host computers has increased in conjunction with the increasing complexity of the examination systems and analyzing systems. In this situation, the data are concentrated in the path from the examination system or analyzing system to the host computer, such that data processing is slowed between the examination system or analyzing system and the host computer. This circumstance inconveniently reduces the processing capacity of the examination system and analyzing system.

Various art has been disclosed for suppressing the reduction of the processing capacity of conventional examination systems and analyzing systems (for example, Japanese Laid-Open Patent Publication No. 11-237384).

Japanese Laid-Open Patent Publication No. 11-237384 discloses a clinical examination system wherein a carrier line unit performs structural control data communications and a processing unit performs functional control data communications and specimen data communications. In the clinical examination system disclosed in Japanese Laid-Open Patent Publication No. 11-237384, data related to the processing unit are transmitted from the processing unit to a host computer, and data related to the carrier line unit are transmitted from the carrier line unit to the host computer, such that transmission to the host computer is distributed through two paths. In this way, the reduction of the processing capability of the clinical examination system is suppressed by suppressing the concentration of data in the transmission path to the host computer compared to when a single path is used to perform transmissions to a host computer.

The clinical examination system disclosed in Japanese Laid-Open Patent Publication No. 11-237384, however, inconveniently concentrates data in a path from the processing unit or carrier line unit to a host computer when the processing unit or carrier line unit is a unit for transmitting large quantities of data. Therefore, for example, when data are concentrated in the path from the carrier line unit to a host computer and an inquiry is issued from the carrier line unit to the host computer, either no response or a delayed response is sent from the host computer, such that there is an inconvenient delay in the processing performed by the clinical examination system. In this case, a problem arises inasmuch as it is difficult to suppress a reduction in the capability of the clinical examination system even when using the clinical examination system disclosed in Japanese Laid-Open Patent Publication No. 11-237384.

Furthermore, in the clinical examination system disclosed in Japanese Laid-Open Patent Publication No. 11-237384, the host computer processes large amounts of data since all information from the processing unit and the carrier line unit are ultimately transmitted to the host computer. In this case as in the previous case the processing of the clinical examination system is delayed when an inquiry or the like is issued from the carrier line unit to the host computer, and as a result it is difficult to suppress a reduction in the capability of the clinical examination system.

Furthermore, in the clinical examination system disclosed in Japanese Laid-Open Patent Publication No. 11-237384, since all information from the carrier line unit or processing unit are transmitted to the host computer, even data that are not necessarily required by the user are disadvantageously transmitted to the host computer.

SUMMARY

The scope of the present invention is defined solely by the appended claims, and is not affected to any degree by the statements within this summary.

First analyzer and analyzing system embodying features of the present invention suppress a reduction in processing capability.

Second analyzer embodying features of the present invention includes a first conveyance device for transporting a container accommodating analyte; a first analyzer body for analyzing analyte accommodated in a container transported by the first conveyance device; a first transmission device for transmitting a first information through a first path from the first conveyance device to a predetermined computer; a second transmission device for transmitting a second information through a second path from the first analyzer body to the predetermined computer without passing through the first conveyance device; and setting device for setting whether or not to transmit the first information to the predetermined computer.

Third analyzer embodying features of the present invention includes a status information acquiring means for acquiring status information representing the status of the analyzer; a setting means for setting whether or not to transmit the status information to a computer which collects analyte analysis results from a plurality of analyzers; a determination means for determining whether or not to transmit the status information based on the setting set by the setting means; and a first transmission means for transmitting status information to the computer based on the determination of the determination means.

Fourth analyzer embodying features of the present invention includes a first conveyance device for transporting a container accommodating analyte; a first analyzer body for analyzing analyte accommodated in a container transported by the first conveyance device; a first transmission means for transmitting a first information from the first conveyance device to a first computer; and a second transmission means for transmitting a second information from the first analyzer body to a second computer; wherein the first information comprises maintenance information including anomaly information generated by at least one among the first analyzer body and first conveyance device.

DETAILED DESCRIPTION OF THE EMBODIMENT

The embodiments of the present invention are described hereinafter based on the drawings.

First Embodiment

Figure 1:
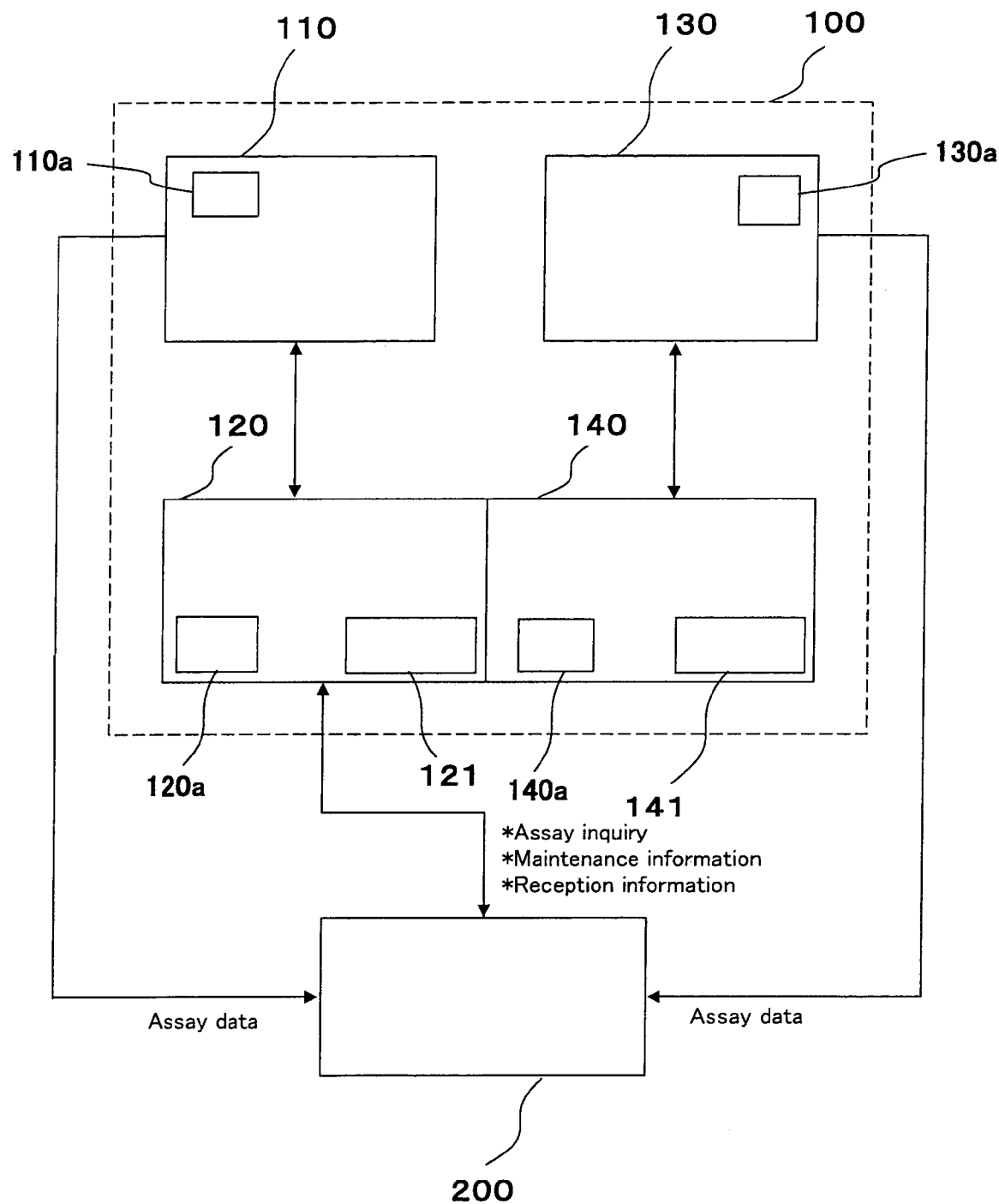
FIG. 1 is a block diagram showing the relationship between a user-side host computer and the analyzing system of a first embodiment of the present invention.
Figure 2:
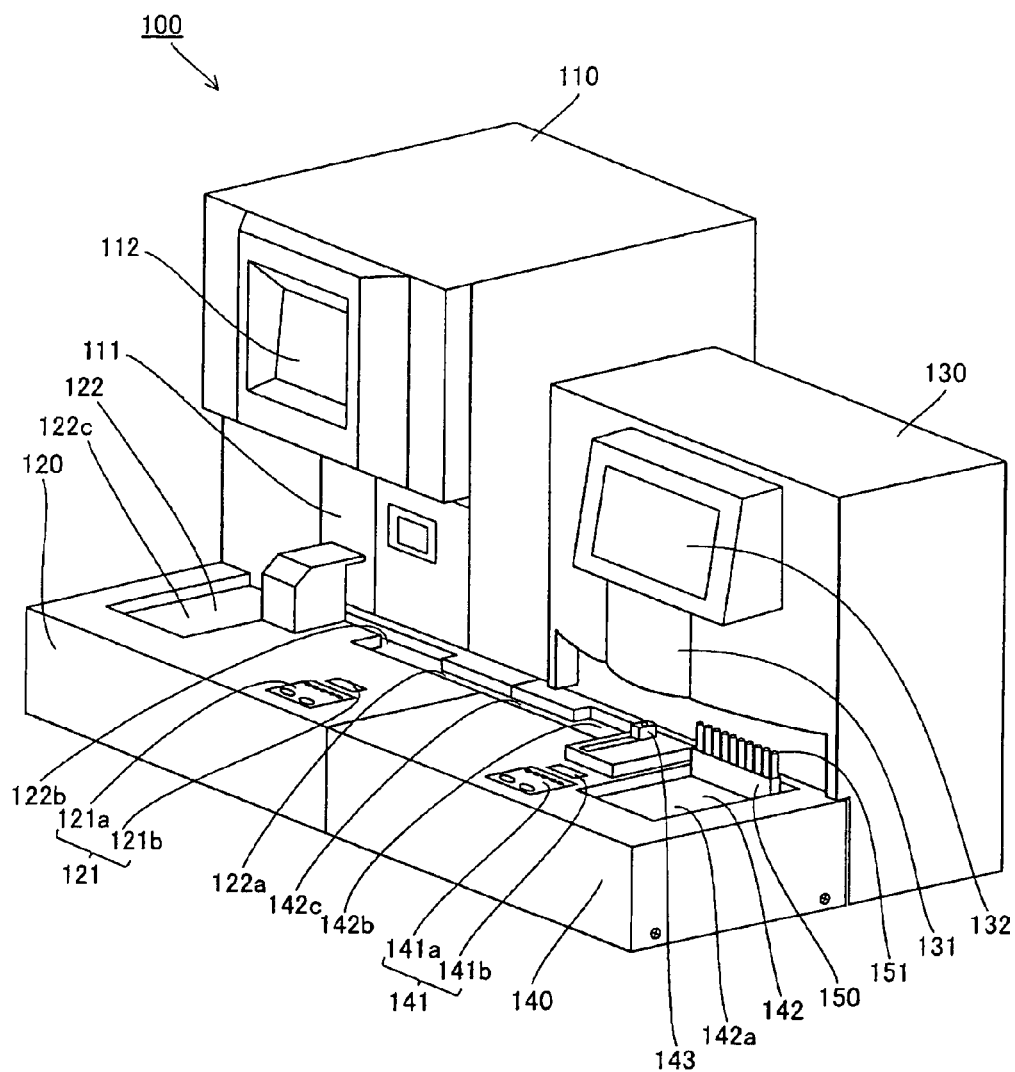
FIG. 2 is a perspective view of the overall structure of the analyzing system of the first embodiment of the present invention.

FIG. 1 is a block diagram showing the relationship between a user-side host computer and the analyzing system of a first embodiment of the present invention, and FIG. 2 is a perspective view of the overall structure of the analyzing system of the first embodiment of the present invention.

First, the general structure of the analyzing system of the first embodiment is described below with reference to FIGS. 1 and 2. The analyzing system 100 of the first embodiment is provided with a first analyzer and a second analyzer. The first analyzer is provided with a body 110, and a first conveyance device 120, as shown in FIG. 1. The second analyzer is provided with a body 130, and a second conveyance device 140. The body 110 is connected to a user-side host computer 200 and the first conveyance device 120, and the body 130 is connected to the user-side host computer 200 and the second conveyance device 140. Furthermore, the first conveyance device 120 is connected to the user-side host computer 200, body 110, and the second conveyance device 140.

The body 110 includes a circuit for communicating information of the host computer 200 and the first conveyance device 120. Furthermore, the body 110 includes a control unit 110a, which includes a CPU, ROM, RAM, and the previously mentioned communication circuit and the like. The first conveyance device 120 includes a circuit for communicating information of the host computer 200, body 110, and the second conveyance device 140. Furthermore, the first conveyance device 120 includes a control unit 120a, which includes a CPU, ROM, RAM, and the previously mentioned communication circuit and the like. The control unit 120a functions as a status information acquiring means for acquiring status information which represents the state of the analyzing system 100, setting means for setting whether or not to transmit status information to the host computer 200 in accordance with information input by a setting unit 121 described later, determination means for determining whether or not to transmit status information based on the setting of the setting means, and a first transmission means for transmitting status information to the host computer 200 based on the determination of the determination means. The body 130 includes a circuit for communicating information with the host computer 200 and the second conveyance device 140, and the second conveyance device 140 includes a circuit for communicating information with the body 130 and the first conveyance device 120. The body 130 includes a control unit 130a which includes a CPU, ROM, RAM, and circuit for communication. Furthermore, the second conveyance device 140 includes a control unit 140a which includes a CPU, ROM, RAM, and circuit for communication.

The body 110 and the body 130 may be, for example, urine analyzers. In this case, as shown in FIG. 2, the body 110 is connected to the back stage of the body 130, and is so disposed to perform further detailed analysis and examination of the urinalysis results of the body 130. The first carrier 120 is a device for automatically supplying specimens to the body 110, and the second conveyance device 140 is a device for automatically supplying specimens to the body 130. Furthermore, the body 110 includes an assay unit 111 and a display unit 112, and the body 130 includes an assay unit 131 and display unit 132.

As shown in FIGS. 1 and 2, in the first embodiment the first conveyance device 120 is provided with a setting unit 121 for setting the operation of the first conveyance device 120, and setting whether or not to transmit maintenance information of the first conveyance device 120 to the host computer 200. As shown in FIG. 2, the setting unit 121 includes an input unit 121a having a plurality of setting keys, and an LCD display 121b as a display unit. Furthermore, the first conveyance device 120 is provided with a conveyance device 122 for transporting a specimen rack 150 which accommodates a plurality (10 in the present embodiment) of specimen containers 151 holding specimens. The conveyance device 122 includes a transport unit 122a, transverse feed unit 122b, and collecting unit 122c.

Furthermore, the second conveyance device 140 includes a setting unit 141 for setting the operation of the second conveyance device 140, transport unit 142 for transporting a specimen rack 150 which accommodates a plurality of specimen containers 151 holding specimens, and an interrupt specimen processing unit 143 used when interrupting the examination of a normal specimen assay. The setting unit 141 includes a key input unit 141a having a plurality of keys, and an LCD display 141b as a display device. The conveyance device 142 includes a transport unit 142a, transverse feed unit 142b, and discharge unit 142c.

Figure 3:
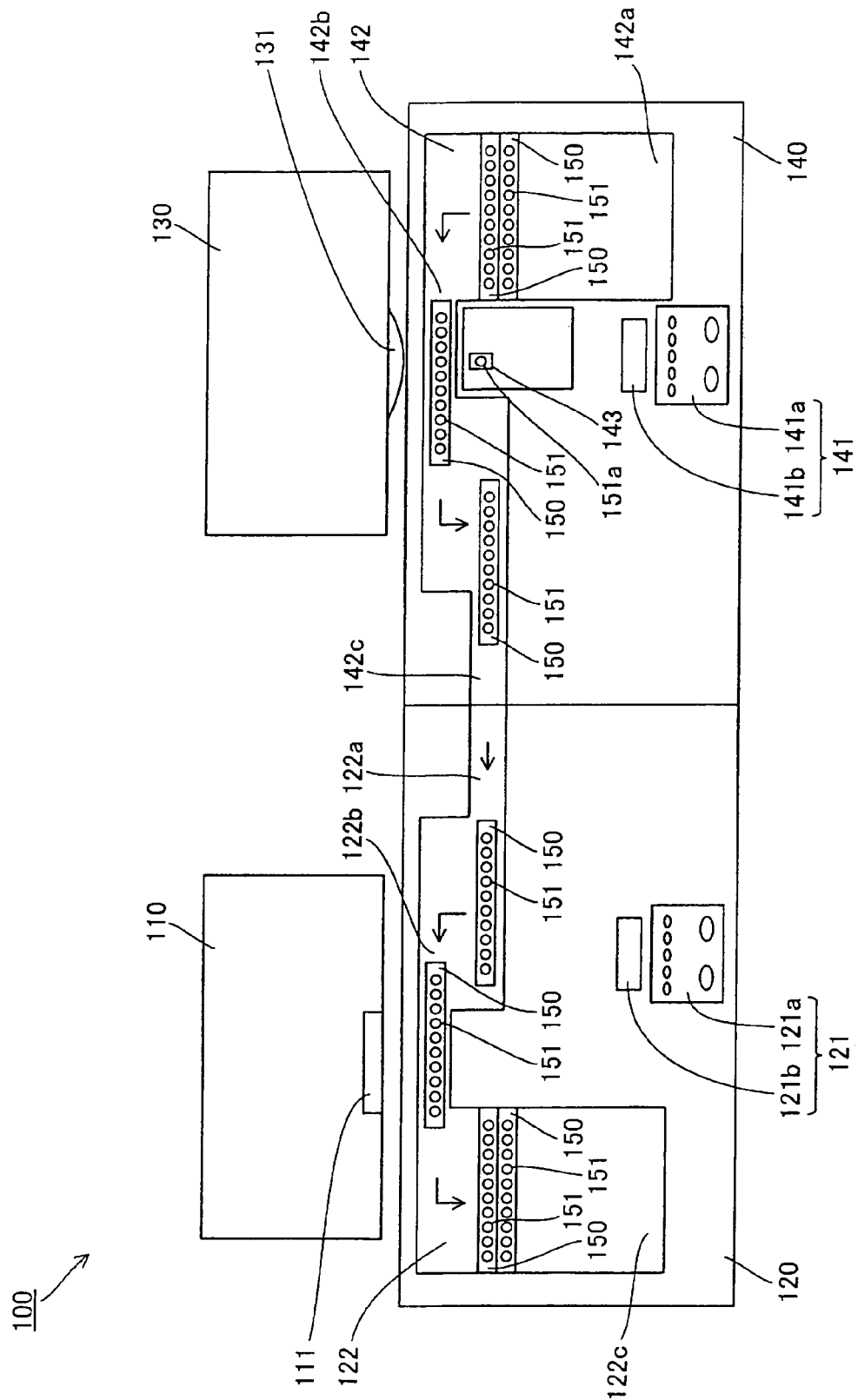
FIG. 3 briefly illustrates the operation of the analyzing system of the first embodiment shown in FIG. 2.
Figure 4:
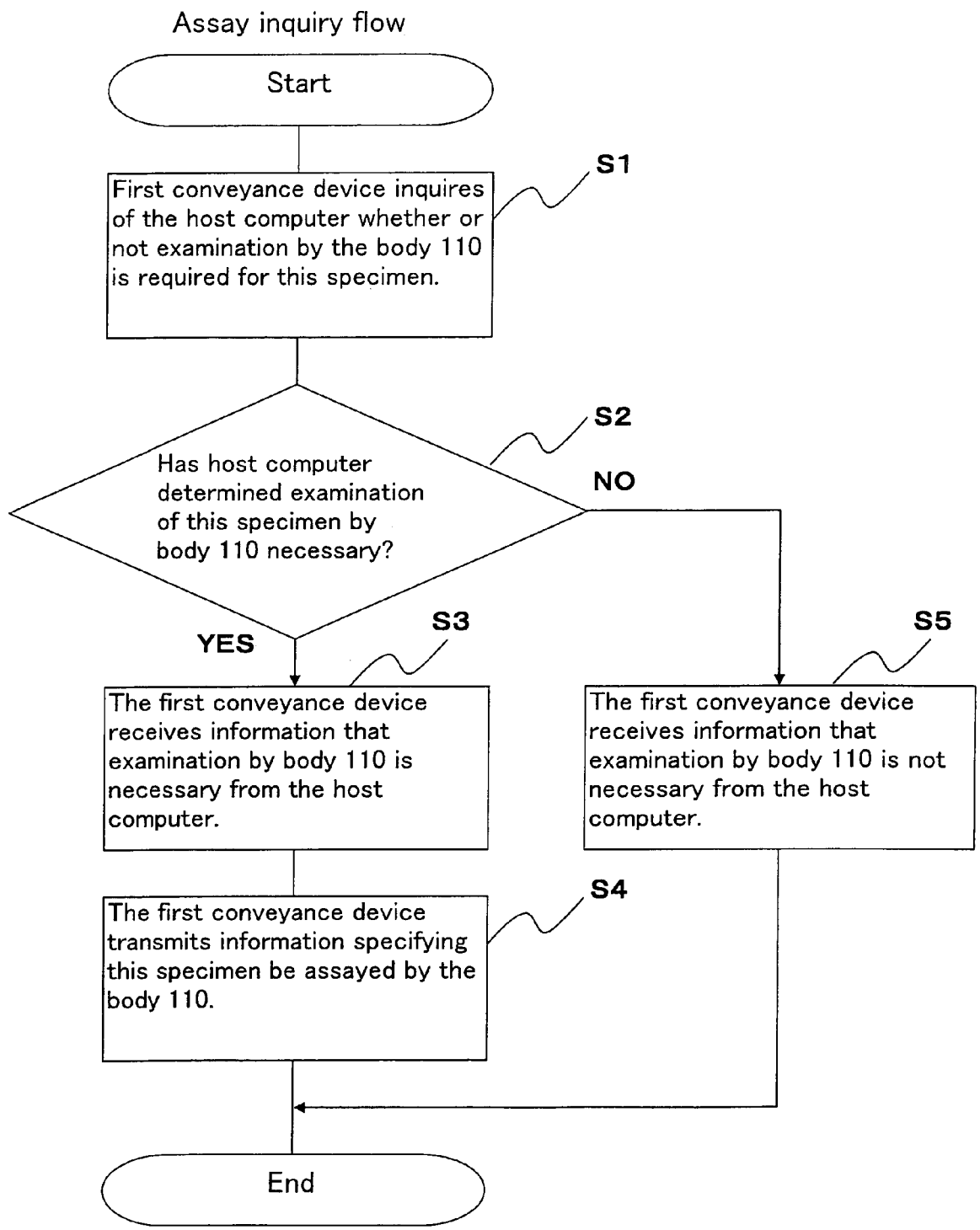
FIG. 4 is a flow chart illustrating the assay inquiry in the analyzing system of the first embodiment shown in FIG. 1.

FIG. 3 briefly illustrates the assay operation of the analyzing system of the first embodiment shown in FIG. 2, and FIG. 4 is a flow chart showing the assay inquiry operation of the analyzing system of the first embodiment shown in FIG. 1. The assay operation of the analyzing system of the first embodiment is described below with reference to FIGS. 1 through 4.

In the analyzing system 100 of the first embodiment, as shown in FIG. 3, a specimen rack 150 accommodating a plurality of specimen containers 151 holding specimens (urine) is automatically transported in the arrow direction. Specifically, the specimen rack 150 accommodating a plurality of specimen containers 151 holding specimens is first placed in the transport unit 142a of the second conveyance device 140. Then, the start key is pressed on the setting unit 141. In this way, the specimen rack 150, which has been placed in the transport unit 142a of the second conveyance device 140 is transported to the transverse feed unit 142b. Next, the specimen rack 150 is transported transversely one specimen container 151 at a time by the transverse feed unit 142b to the assay unit 131 of the body 130. In the assay unit 131 of the body 130, all the specimens held in the specimen containers 151 accommodated in the rack 150 are sequentially assayed. Then, the body 130 transmits the specimen assay data to the host computer 200 (refer to FIG. 1). Furthermore, after the specimen rack 150 is transported from the transverse feed unit 142b to the discharge unit 142c, the specimen rack 150 is transported to the transport unit 122a of the first conveyance device 120. Thereafter, the first conveyance device 120 detects the arrival of the specimen rack 150 at the transport unit 122a, and begins the operation.

The specimen rack 150, which has arrived at the transport unit 122a of the first conveyance device 120, is transported to the transverse feed unit 122b of the first conveyance device 120. Thereafter, the specimen rack 150 is transported transversely one specimen container 151 at a time by the transverse feed unit 122b to the assay unit 111 of the body 110. In the assay unit 111 of the body 110, an assay is performed on only those specimens which have been determined to require detailed urinalysis by the body 110 based on the urinalysis result of the body 130.

The assay inquiry operation for determining whether or not to assay a specimen by the body 110 is described below with reference to FIG. 4. The assay inquiry operation is performed by controller 120a of the first conveyance device 120. First, in step 1 (S1), the first conveyance device 120 sends an inquiry to the host computer 200 as to whether or not examination of the specimens is required by the body 110. This inquiry occurs while the specimen containers 151 of the specimen rack 150, which have been assayed in the assay unit 131 of the body 130, are transported to the assay unit 111 of the body 110. Then, in step 2 (S2), the host computer 200 determines whether or not the specimens require examination by the body 110 based on the assay data of the body 130. When the host computer 200 determines the specimens require examination by the body 110, in step 3 (S3), the first conveyance device 120 receives information that examination by body 110 is necessary from the host computer 200. In step 4 (S4), the first conveyance 120 transmits information specifying the specimen assay to the body 110. In this case, the specimens are assayed in the assay unit 111 of the body 110. When the host computer determines in step 2 that the specimens do no require examination by the body 110, then in step 5 (S5), the first conveyance device 120 receives information that examination by body 110 is not necessary from the host computer 200. In this case, the specimens are not assayed in the assay unit 111 of the body 110.

As described above, the assay unit 111 of the body 110 assays only those specimens determined to require detailed urinalysis by the body 110 based on the urinalysis results of the body 130. Then, the assay data of the specimens assayed by the assay unit 111 of the body 110 are transmitted from the body 110 to the host computer 200, as shown in FIG. 1. The assay data transmitted from the body 110 to the host computer 200 include graphic data such as large-quantity scatter data and the like.

Thereafter, the specimen rack 150 is transported from the transverse feed unit 122b to the collection unit 122c, as shown in FIG. 3. When the specimen rack 150 has arrived at the collection unit 122c, the information of the specimen rack 150 is transmitted as collection information from the first conveyance device 120 to the host computer 200, as shown in FIG. 1. The above operation is performed sequentially for each specimen rack 150.

When a normal specimen assay is interrupted to perform an interrupt assay using the specimen track 150, the stop key of the setting unit 141 is pressed and the specimen container 151a holding the specimen is placed in the interrupt specimen processing unit 143, as shown in FIG. 3.

Then, the specimen held in the specimen container 151a is assayed by the assay unit 131 of the body 130.

Details of the maintenance information in the first embodiment are described below. Maintenance information in the first embodiment is information used during maintenance, and includes information described in points (1) through (10) below.

That is, the maintenance information includes (1) information indicating the current status of the body 110, first conveyance device 120, body 130 and second conveyance device 140 (line information), (2) position information of the specimen rack 150 on the conveyor line (line position information), (3) information relating to the content of key input by the setting unit 121 of the first conveyance device 120 and the setting unit 141 of the second conveyance device 140 (conveyance device operating information), (4) information relating to send/receive history of assay-related commands relative to the body 110 and body 130 of the first conveyance device 120 and second conveyance device 140 (device send/receive information), (5) reset completion information of the interrupt and specimen rack 150 (rack management information), (6) system setting information of the first conveyance device 120 and second conveyance device 140 (system setting information), (7) error information of the body 110 and body 130 (analyzer anomaly information), (8) program version information of the first conveyance device 120 and second conveyance device 140 (program information), (9) device ID and program information of the body 110 and body 130 (device program information), (10) error generation and restoration information in the first conveyance device 120 and second conveyance device 140 (error information).

The line information is information representing the current operating state of the analyzing system 100, and includes information expressing when the analyzing system 100 is in standby and not operating, information expressing when the system is operating normally, and information expressing when an anomaly has occurred and the system has stopped.

The line information (1) is transmitted when a change of state is generated in the body 110, first conveyance device 120, body 130, and second conveyance device 140. The rack position information (2) is transmitted when the rack position of the specimen rack 150 is changed. The conveyance device operating information (3) is transmitted when there is setting key input by the setting unit 121 of the first conveyance device 120 and the setting unit 141 of the second conveyance device 140. The device send/receive information (4) is transmitted when an assay related command is transmitted and when an assay result command is received by the body 110 and body 130 of the first conveyance 120 and the second conveyance 140. The rack management information of (5) is transmitted when an interrupt is generated by stop key input on the setting unit 121 of the first conveyance device 120 and setting unit 141 of the second conveyance device 140, or reset of the specimen rack 150 is completed.

The system setting information (6) is transmitted when there is a change in the system setting of the first conveyance device 120 or second conveyance device 140, and when communication is established between the first conveyance device 120 and the host computer 200. The analyzer anomaly information (7) is transmitted when an anomaly is generated in the body 110 or body 130. The program information (8) is transmitted when communication is established between the first conveyance device 120 and the host computer 200. The device program information (9) is transmitted when the body 110 and body 130 are actuated, or when communication is established between the first conveyance device 120 and the host computer 200. The error information (10) is transmitted when an anomaly (error) is generated in the first conveyance device 120 or second conveyance device 140.

Figure 5:
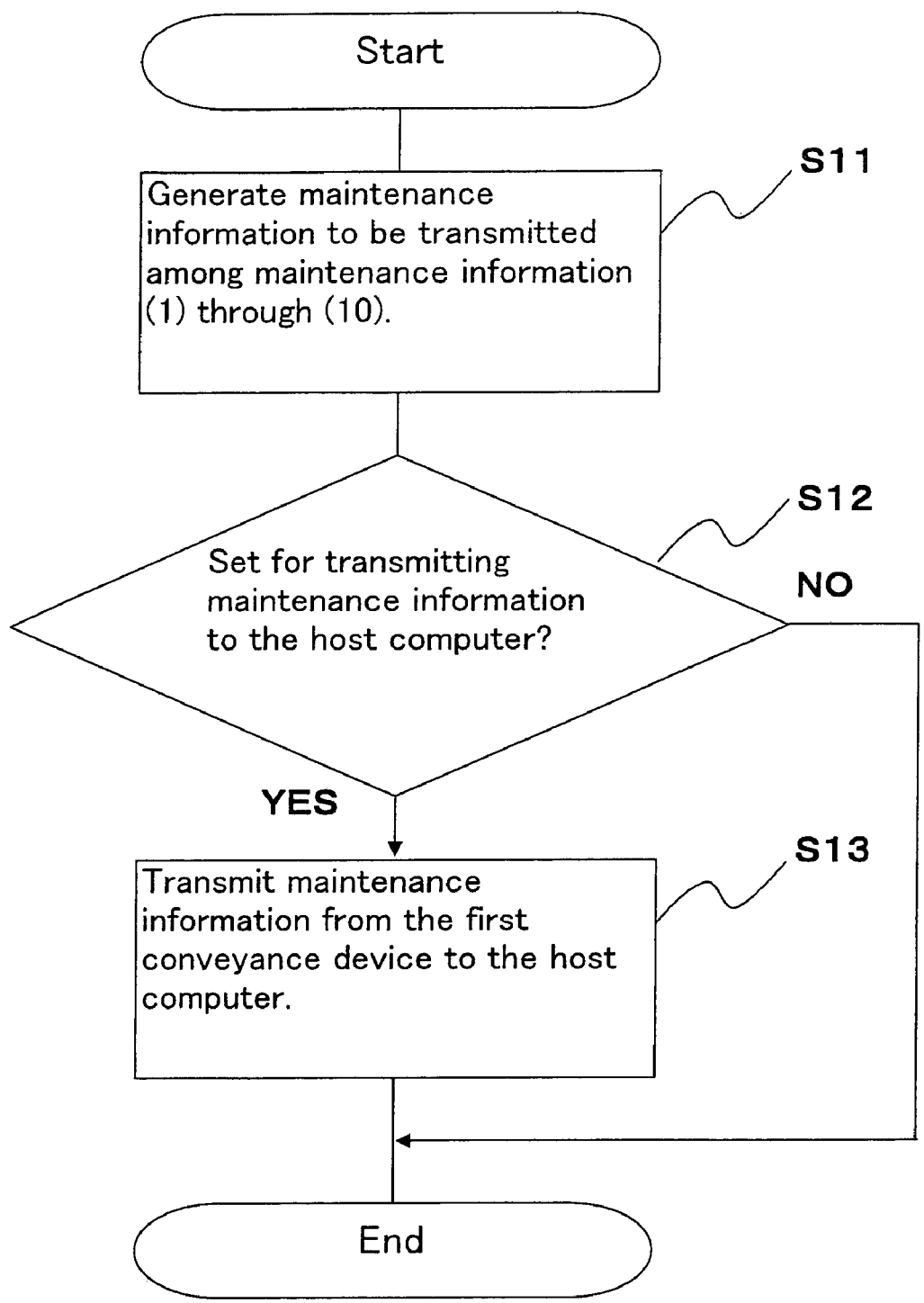
FIG. 5 is a flow chart showing the transmission sequence of maintenance information in the analyzing system of the first embodiment shown in FIG. 1.

In the analyzing system 100 of the first embodiment described above, it is possible to set whether or not to transmit maintenance information (1) through (10) from the first conveyance device 120 to the host computer 200 using the setting unit 121 of the first conveyance device 120. FIG. 5 is a flow chart illustrating the sequence of transmission of the maintenance information in the analyzing system of the first embodiment shown in FIG. 1.

The transmission sequence of the maintenance information (1) through (10) is described below with reference to FIG. 5. The transmission sequence of the maintenance information is performed by controller 120a of the first conveyance device 120. First, when maintenance information among the maintenance information (1) through (10) are generated for transmission in step 11 (S11), then a determination is made in step 12 (S12) as to whether or not transmission of maintenance information to the host computer 200 has been set. When it is determined that transmission of maintenance information to the host computer 200 has been set, the maintenance information is sent from the first conveyance device 120 to the host computer 200 in step 13 (S13). When maintenance information is received, the host computer 200 only saves the information as a maintenance log, and does not perform a special operation. When it is determined in step 12 (s12) that transmission of maintenance information to the host computer 200 has not been set, the maintenance information is not sent to the host computer 200 and the routine ends.

By providing the setting unit 121 for setting whether or not to transmit the maintenance information (1) through (10) from the first conveyance device 120 to the host computer 200 in the analyzing system 100 of the first embodiment, if maintenance information (1) through (10) is set in the setting unit 121 so as to not be transmitted to the host computer 200, it is possible to suppress concentration of data in the path from the first conveyance device 120 to the host computer 200 and reduce the amount of data processing performed by the host computer 200. In this way it is possible to suppress a lack of response or delayed response from the host computer 200 when the first conveyance device 120 transmits an inquiry as to whether or not analysis is required by the body 110 to the host computer 200. As a result, it is possible to suppress a reduction in the processing capability of the analyzing system 100 since assay processing delays in the body 110 are suppressed. Furthermore, if the setting unit 121 is set so as to permit transmission of maintenance information from the first conveyance device 120 to the user-side host computer 200, anomalies can be easily analyzed since maintenance information stored in the user-side host computer 200 can be analyzed when maintenance is performed.

By providing the setting unit 121 for setting whether or not to transmit maintenance information from the first conveyance 120 to the host computer 200 in the first embodiment, it is possible to actuate a setting so as to not transmit maintenance information from the first conveyance device 120 to the user-side host computer 200 when the user does not require maintenance information, and to actuate a setting so as to transmit maintenance information from the first conveyance device 120 to the user-side host computer 200 when the user does require maintenance information.

Furthermore, since the first embodiment is constructed such that the first conveyance device 120 inquires of the host computer 200 as to whether or not assay by the body 110 is necessary, assays are easily performed only for specimens requiring analysis by the body 110 based on the inquiry to the host computer 200.

(Second Embodiment)

Figure 6:
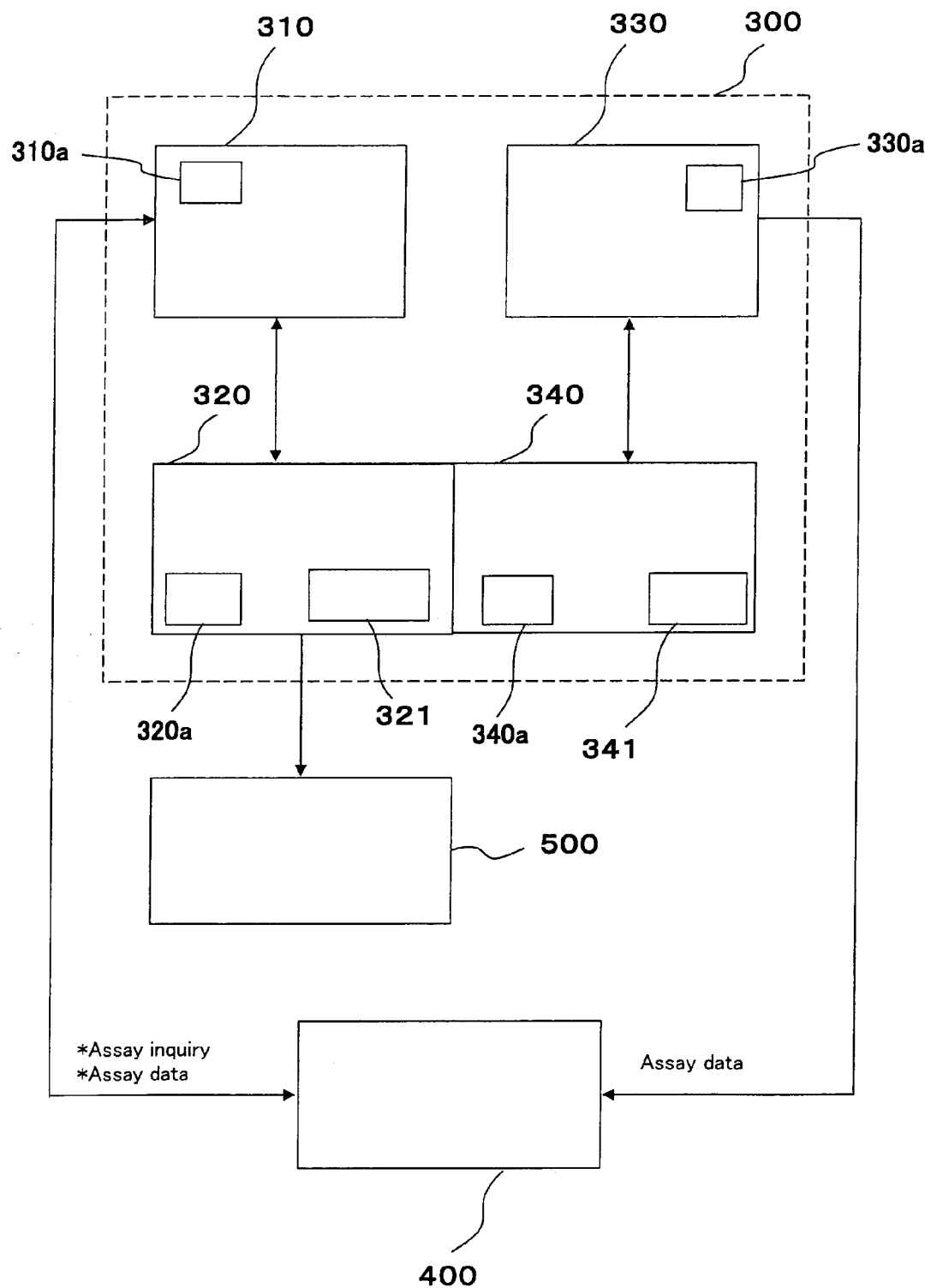
FIG. 6 is a block diagram showing the relationships among a maintenance PC, user-side host computer, and analyzing system of a second embodiment of the present invention.

FIG. 6 is a block diagram showing the relationships among the maintenance PC, user-side host computer, and analyzing system of a second embodiment of the present invention. The transmission of maintenance information to the maintenance PC in the second embodiment is described in terms of aspects which differ from the first embodiment based on FIG. 6.

An analyzing system 300 of the second embodiment is provided with a first analyzer and second analyzer. The first analyzer is provided with a body 310 and first conveyance device 320. The second analyzer is provided with a body 330 and second conveyance device 340. The body 310, first conveyance 320, body 330 and second conveyance 340 have the same structures as the body 110, first conveyance 120, body 130, and second conveyance 140 of the first embodiment. The setting unit 321 of the first conveyance device 320 in the second embodiment differs from that of the first embodiment inasmuch as it can only set the operation settings of the first conveyance device 320, and cannot set whether or not to transmit maintenance information to the maintenance PC 500. The setting unit 341 of the second conveyance device 340 performs the operation setting of the second conveyance device 340 similar to the first embodiment.

The body 310 is connected to a user-side host computer 400 and the first conveyance device 320, and the body 330 is connected to the user-side host computer 400 and the second conveyance device 340.

In the second embodiment, the first conveyance device 320 is connected to the maintenance PC 500, body 310, and second conveyance device 340.

In the second embodiment, the body 310 includes a circuit for communicating information with the host computer 400 and the first conveyance device 320. Furthermore, the body 310 includes a control unit 310a, which includes a CPU, ROM, RAM, and the previously mentioned communication circuit and the like. The first conveyance device 320 includes a circuit for communicating with the body 310 and second conveyance device 340. The first conveyance device 320 includes a control unit 320a, which includes a CPU, ROM, RAM, and the previously mentioned communication circuit. The body 330 includes a circuit for communicating information with the host computer 400 and the second conveyance device 340, and the second conveyance device 340 includes a circuit for communicating information with the body 330 and the first conveyance device 320. The body 330 includes a control unit 330a, which includes a CPU, ROM, RAM, and the previously mentioned communication circuit. Furthermore, the second conveyance device 340 includes a control unit 340a, which includes a CPU, ROM, RAM, and the previously mentioned communication circuit.

In the second embodiment, the maintenance information (1) through (10) are transmitted from the first conveyance device 320 to the maintenance PC 500, similar tot he first embodiment. In the second embodiment, an inquiry as to whether or not a specimen assayed by the body 330 must be assayed by the body 310 is sent from the body 310 to the host computer 400. The respective assay data are transmitted from the body 310 and body 330 to the host computer 400. In the second embodiment, unlike the first embodiment, the assay data transmitted from the body 310 to the host computer 400 does not include large-quantity scatter data.

The assay operation of the analyzing system 300 of the second embodiment is identical to the assay operation of the analyzing system 100 of the first embodiment.

The transmission of maintenance information in the second embodiment is described in detail below with reference to FIGS. 6 through 9. The transmission sequence of maintenance information is performed by the controller 320*a* of the first conveyance device 320. Regarding the transmission sequence of maintenance information in the second embodiment, maintenance information (1) through (10) similar to the first embodiment are transmitted from the first conveyance device 320 to the host computer 400 when maintenance information (1) through (10) are transmitted. In the second embodiment, the maintenance information (1) through (10) are invariably transmitted from the first conveyance device 320 to the maintenance PC 500 since there is no setting unit provided to set whether or not to transmit the maintenance information (1) through (10) to the maintenance PC 500.

Figure 7:
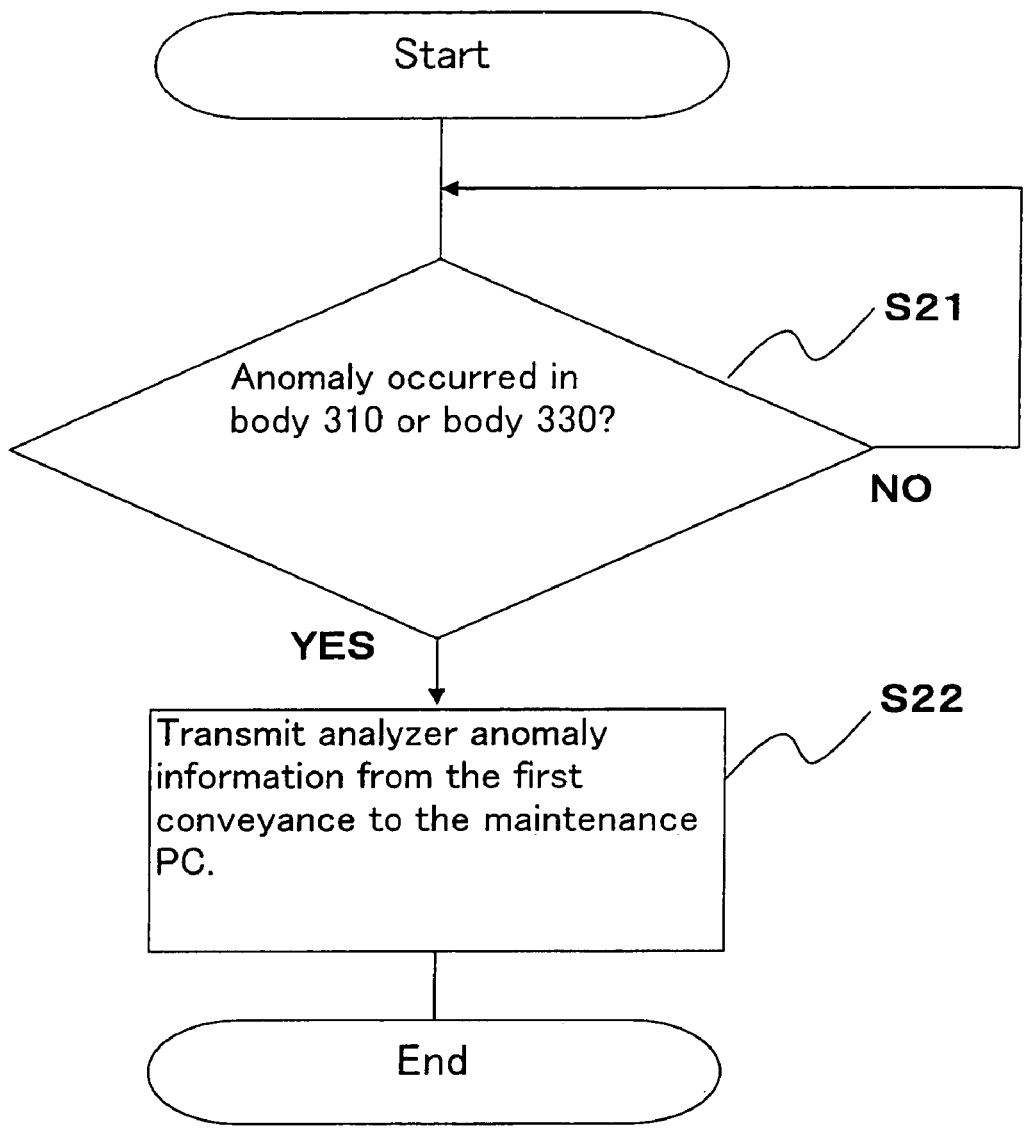
FIG. 7 is a flow chart showing the transmission flow of analyzer anomaly information in the analyzing system of the second embodiment shown in FIG. 6.

For example, the transmission flow of analyzer anomaly information (7) expressing the generation of an anomaly (error) in the body 310 or body 330 among the maintenance information (1) through (10), is shown in FIG. 7; in step 21 (S21), a determination is made as to whether or not an anomaly has occurred in the body 310 or body 330. When it has been determined that an anomaly has occurred in the body 310 or body 330 in step 21, then the analyzer anomaly information (7) is transmitted from the first conveyance device 320 to the maintenance PC 500 in step 22 (S22). That is, when it is determined that an anomaly has occurred in the body 310, the analyzer anomaly information relating to the body 310 is transmitted from the body 310 to the maintenance PC 500 through the first conveyance device 320. When it is determined that an anomaly has occurred in the body 330, analyzer anomaly information relating to the body 330 is transmitted from the body 330 to the maintenance PC 500 through the second conveyance device 340 and the first conveyance device 320. Furthermore, when it has been determined that an anomaly has not occurred in the body 310 or body 330 in step 21, step 21 is repeated again. The maintenance PC 500 which receives the analyzer anomaly information stores the reception time and analyzer anomaly information in memory.

Figure 8:
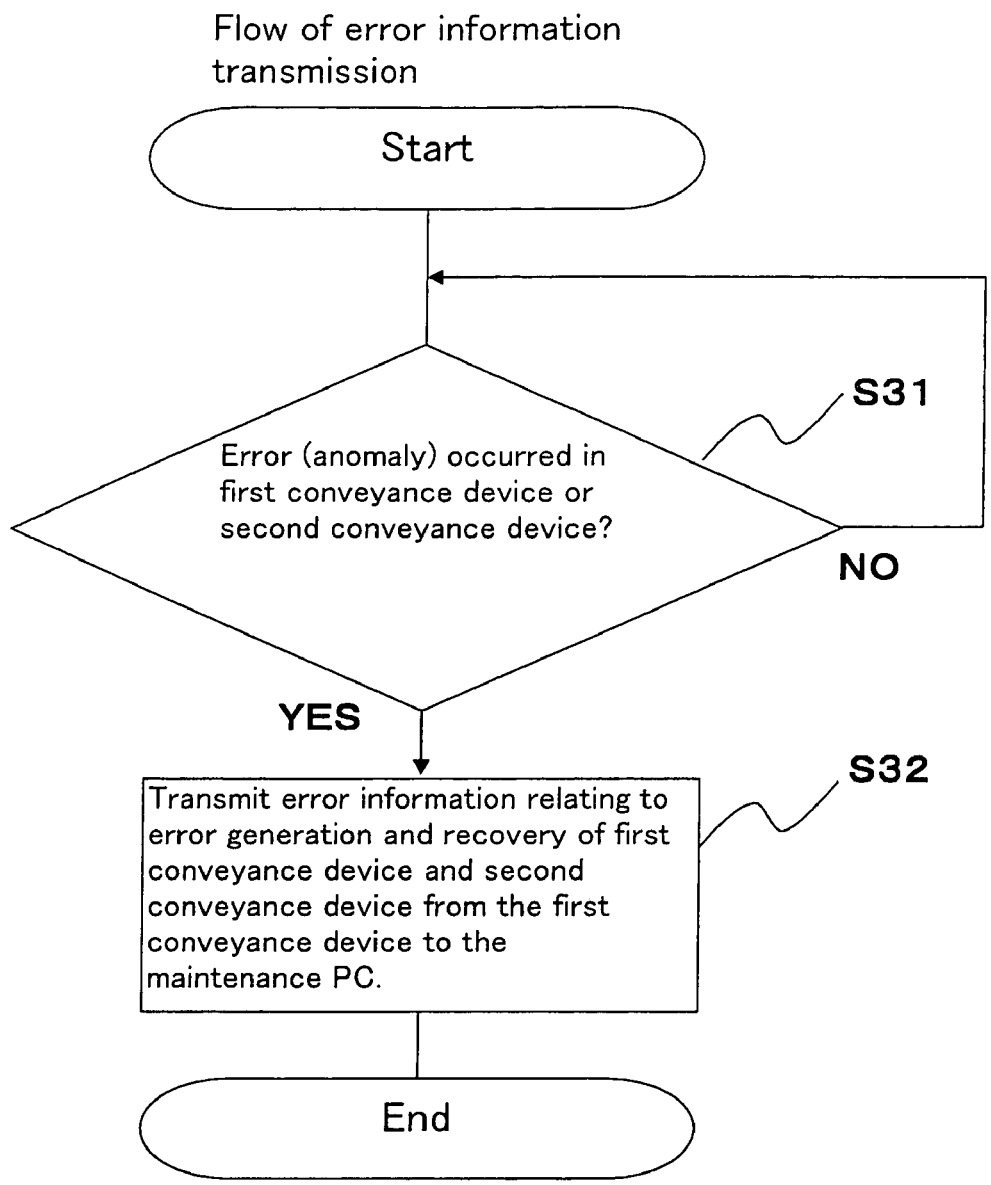
FIG. 8 is a flow chart showing the transmission flow of error information in the analyzing system of the second embodiment shown in FIG. 6.

Error information including error generation and recovery (10) in the first conveyance device 320 and second conveyance device 340 among the maintenance information is transmitted to the first conveyance device 320 or second conveyance device 340 when an error (anomaly) is generated. The transmission sequence of error information is performed by the controller 320*a* of the first conveyance device 320. The transmission flow in this case is shown in FIG. 8; in step 31 (S31), a determination is made as to whether or not an error (anomaly) has been occurred in the first conveyance device 320 or second conveyance device 340. When it is determined that an error has occurred in the first conveyance 320 or second conveyance 340 in step 31, then error information including error generation and recovery information (10) is transmitted from the first conveyance device 320 to the maintenance PC 500 in step 32 (S32). That is, when it is determined that an error has occurred in the first conveyance device 320, information relating to the error generation and recovery in the first conveyance device 320 is transmitted to the maintenance PC 500 from the first conveyance device 320. When is determined that an error has occurred in the second conveyance device 340, information relating to the error generation and recovery in the second conveyance device 340 is transmitted from the second conveyance device 340 to the maintenance PC 500 through the first conveyance device 320. Furthermore, when it is determined that an error has not occurred in the first conveyance device 320 or second conveyance device 340 in step 31, step 31 is repeated again. The maintenance PC 500 which received the error information, stores the reception time and error information in memory.

Figure 9:
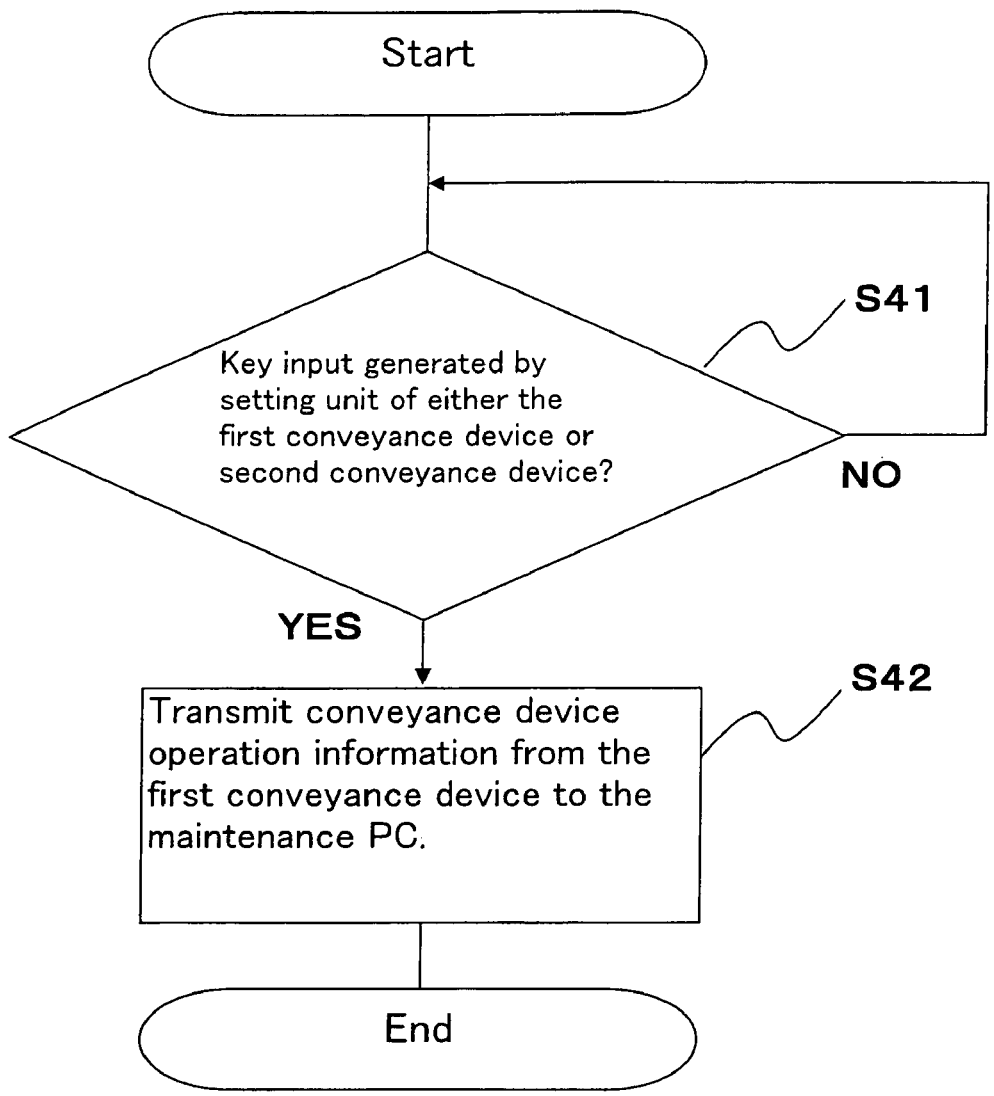
FIG. 9 is a flow chart showing the transmission flow of the conveyance device operation information in the analyzing system of the second embodiment shown in FIG. 6.

The transmission flow of conveyance device operating information relating to the key input content of the setting unit 321 of the first conveyance device 320 and the setting unit 341 of the second conveyance device 340 (3) among the maintenance information is shown in FIG. 9. The transmission sequence of conveyance device operating information is performed by the controller 320*a* of the first conveyance device 320. In step 41 (S41), a determination is made as to whether or not key input has occurred in the setting unit 321 of the first conveyance device 320 or the setting unit 341 of the second conveyance device 340. When it is determined that key input has occurred in step 41, conveyance device operating information is transmitted from the first conveyance device 320 to the maintenance PC 500. That is, when it is determined that there has been key input in the setting unit 321 of the first conveyance device 320, the conveyance device operating information relating to the first conveyance device 320 is transmitted from the first conveyance device 320 to the maintenance PC 500. When it is determine that key input has occurred in the setting unit 341 of the second conveyance device 340, conveyance device operating information relating to the second conveyance device is transmitted from the second conveyance device 340 to the maintenance PC 500 through the first conveyance device 320. When it is determined that key input has not occurred in the setting unit 321 of the first conveyance device 320 or the setting unit 341 of the second conveyance device 340 in step 41, step 41 is repeated again. The maintenance PC 500, which received the conveyance device operating information, stores the reception time and conveyance device operating information in memory.

In the second embodiment, anomaly information relating to the body 310, body 330, first conveyance device 320, and second conveyance device 340 can be easily managed by the maintenance PC 500 by transmitting maintenance information which includes anomaly information (analyzer anomaly information and error information) generated by the body 310, body 330, first conveyance device 320, and second conveyance device 340 from the first conveyance device 320 to the maintenance PC 500. In this way maintenance efficiency is improved since anomaly information (analyzer anomaly information and error information) stored in the maintenance PC 500 can be analyzed during maintenance.

In the second embodiment, anomaly information can be managed by the maintenance PC 500 in real time by transmitting anomaly information (analyzer anomaly information and error information) from the first conveyance device 320 to the maintenance PC 500 when an anomaly occurs in the first conveyance device 320 or the second conveyance device 340.

In the second embodiment, maintenance efficiency is improved because the occurrence of an anomaly can be confirmed in either of the first conveyance device 320 or second conveyance device 340 during operation when a service engineer analyzes the maintenance PC 500 by including conveyance device operating information (3) representing the operating history of the first conveyance device 320 and second conveyance device 340 as maintenance information transmitted from the first conveyance device 320 to the maintenance PC 500.

In the second embodiment, data concentration to the host computer 400 can be suppressed unlike when maintenance information, assay data, and inquiries are transmitted to the host computer 400 since the transmitted data are dispersed to the maintenance PC 500 and the host computer 400 by transmitting the maintenance information to the maintenance PC 500. In this way a lack of response or delayed response from the host computer 400 can be suppressed even when inquiries pertaining to the need for analysis by the body 310 are transmitted from the body 310 to the host computer 400 since the amount of data processing by the host computer 400 is reduced. As a result, a reduction in the processing capacity of the analyzing system 300 can be suppressed since factors delaying assay processing by the body 310 are suppressed.

In the second embodiment, having large amounts of data in the path from the body 310 to the host computer 400 can be suppressed by transmitting assay data which do not include scatter data from the body 310 to the host computer 400. In this way lack of response or delayed response from the host computer 400 can be suppressed even when assay requests as to whether or not an assay is required in the body 310 are issued from the body 310 to the host computer 400. In this way reduction of the processing capability of the analyzing system 300 can be suppressed by suppressing a delay in assay processing in the body 310.

In the second embodiment, maintainability by a maintenance engineer is improved since maintenance information can be managed without using the user-side host computer 400 by providing a maintenance PC 500 specifically for managing maintenance information.

Furthermore, specimen assay results can be easily managed on the user side by transmitting assay data of the body 310 and body 330 to the host computer 400.

The embodiments disclosed herein should be considered as examples in all aspects and not limiting. The scope of the present invention is expressed in the scope of the claims and not described the embodiments, and may be variously modified insofar as such modifications are within the scope and equivalent meaning of the scope of the claims.

For example, although the first and second embodiments describe examples wherein the present invention is applied to analyzing systems which include urine analyzers and conveyance devices, the present invention is not limited to these arrangements and may be applied, for example, to analyzing systems which include conveyance devices and other analyzers, such as blood analyzers and the like.

Although setting whether or not to transmit maintenance information from the first conveyance device to the host computer is accomplished by a setting unit provided in the first conveyance device in the first embodiment, the present invention is not limited to this arrangement, inasmuch as the setting may be performed in the body.

Although setting whether or not to transmit all maintenance information to the host computer is accomplished by a setting unit provided in the first conveyance device in the first embodiment, the present invention is not limited to this arrangement inasmuch as the maintenance information may be grouped and a setting whether or not to transmit each group to the host computer may be accomplished. For example, information relating to the body and information relating to the first and second conveyance devices may be grouped a setting whether or not to transmit each group individually from the first conveyance device to the host computer may be accomplished.

Although settings for whether or not to transmit only maintenance information from the first conveyance device to the host computer can be accomplished in the first embodiment, the present invention is not limited to this arrangement inasmuch as setting whether or not to transmit reception information and assay inquiries in addition to the maintenance information to the host computer may also be accomplished. Reception information is information representing which specimen containers 151 have been collected in the collection unit 122c (FIG. 2).

Although examples in which setting whether or not to transmit maintenance information to the maintenance PC 500 cannot be accomplished in the second embodiment, the present invention is not limited to this arrangement inasmuch as setting whether or not to transmit maintenance information to the host computer may be accomplished. In this case, a reduction in processing capability can be restrained to lowest required limit because maintenance information can be transmitted to the maintenance PC 500 only when necessary, such as when multiple anomalies occur in the device.

Although analyzer anomaly information and error information are transmitted from the first conveyance device to the maintenance PC when an anomaly occurs in the body, first conveyance device and second conveyance device in the second embodiment, the present invention is not limited to this arrangement inasmuch as log files containing the anomaly history of the body, first conveyance device and second conveyance device may be prepared without transmitting the anomaly information at the time the anomaly occurs in the body, first conveyance device and second conveyance device, so as to transmit the log file from the first conveyance device to the maintenance PC at a predetermined time. In this case, the maintenance efficiency can be even more improved because the service engineer can confirm the type and time of anomalous occurrences in the analyzing system. furthermore, a reduction in the processing capability of the first conveyance device can be suppressed because the number of communications is reduced between the first conveyance device and the maintenance PC.

Although assay data which do not include scatter data are transmitted from the body 310 to the host computer 400 in the second embodiment, the present invention is not limited to this arrangement inasmuch as assay data which includes scatter data may be transmitted from the body 310 to the host computer 400.

What is claimed is:

1. An analyzer comprising:
    a first conveyance device for transporting a container accommodating an analyte;
    a first analyzer body for analyzing the analyte accommodated in the container transported by the first conveyance device;
    a first controller in communication with the first conveyance device for controlling the first conveyance device, the first controller comprising a first transmission device in communication with a predetermined computer through a first path for transmitting a first information from the first conveyance device to the predetermined computer;
    a second controller in communication with the first analyzer body for controlling the first analyzer body, the second controller comprising a second transmission device in communication with the predetermined computer through a second path for transmitting a second information from the first analyzer body to the predetermined computer without passing through the first conveyance device, the second transmission device being configured for communication with the first transmission device; and
    a setting device in communication with the first controller for setting whether or not the first transmission device transmits the first information to the predetermined computer;
    wherein the first information comprises:
    information transmitted from the first analyzer body to the predetermined computer through the first conveyance device; and information transmitted from the first conveyance device itself to the predetermined computer.

2. The analyzer of claim 1, wherein the setting device is provided in the first conveyance device and comprises a setting receiver for receiving settings as to whether or not to transmit the first information to the predetermined computer.

3. The analyzer of claim 1, wherein the first information comprises maintenance information for use during maintenance.

4. The analyzer of claim 1, wherein the second information comprises an analyte analysis result.

5. An analyzing system comprising:
the analyzer of claim 1;
a second conveyance device for transporting the container accommodating the analyte; and
a second analyzer body for analyzing the analyte accommodated in the container transported by the second conveyance device, the second analyzer body being configured for transmitting an analyte analysis result to the predetermined computer;
wherein the predetermined computer is in communication with the second analyzer body and is configured to determine whether or not the analyte requires analysis by the first analyzer body based on the analysis result transmitted by the second analyzer body;
the first controller being configured to inquire the predetermined computer whether or not analysis is required to be conducted by the first analyzer body for the analyte; and
the first analyzer body being configured to only analyze the analyte requiring analysis based on the result of the inquiry from the first controller to the predetermined computer, the result of the inquiry being sent from the predetermined computer to the second controller communicating with the first analyzer body.

6. The analyzing system of claim 5, further comprising:
a third controller in communication with the second conveyance device for controlling the second conveyance device, the third controller comprising a third transmission device in communication with the second analyzer body, the predetermined computer and the first transmission device through a third path for transmitting a third information from either one of the second analyzer body and the second conveyance device to the first conveyance device;
wherein the third information comprises information transmitted from the second analyzer body to the first conveyance device through the second conveyance device, and information transmitted from the second conveyance device itself to the first conveyance device.

7. The analyzing system of claim 6, wherein the third controller is incorporated in the second conveyance device.

8. The analyzer of claim 1, wherein the first controller is incorporated in the first conveyance device.

9. The analyzer of claim 1, wherein the second controller is incorporated in the first analyzer body.

* * * * *